United States Patent
Widzgowski

(10) Patent No.: US 9,476,766 B2
(45) Date of Patent: Oct. 25, 2016

(54) METHOD AND APPARATUS FOR EXAMINING A SAMPLE

(71) Applicant: Leica Microsystems CMS GmbH, Wetzlar (DE)

(72) Inventor: Bernd Widzgowski, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 341 days.

(21) Appl. No.: 13/691,382

(22) Filed: Nov. 30, 2012

(65) Prior Publication Data

US 2013/0140437 A1    Jun. 6, 2013

(30) Foreign Application Priority Data

Dec. 1, 2011   (DE) .................. 10 2011 055 945

(51) Int. Cl.
  *G01J 1/44*   (2006.01)
  *G02B 21/00*  (2006.01)
  *G01N 21/64*  (2006.01)

(52) U.S. Cl.
  CPC ............ *G01J 1/44* (2013.01); *G01N 21/6408* (2013.01); *G01N 21/6458* (2013.01); *G02B 21/0076* (2013.01); *G02B 21/0084* (2013.01)

(58) Field of Classification Search
  CPC . G01J 1/44; G01N 21/6408; G01N 21/6458; G02B 21/0076; G02B 21/0084

USPC ................ 250/201.3, 234; 356/445
See application file for complete search history.

(56) References Cited

U.S. PATENT DOCUMENTS

| 5,909,278 | A |   | 6/1999  | Deka et al. |
|-----------|---|---|---------|-------------|
| 6,137,584 | A | * | 10/2000 | Seidel et al. .................. 356/445 |
| 7,859,673 | B2| * | 12/2010 | Moehler et al. ............... 356/445 |
| 2005/0230610 | A1 | * | 10/2005 | Schreiber ....................... 250/234 |
| 2009/0095911 | A1 | * | 4/2009 | Kim et al. ................ 250/363.01 |

FOREIGN PATENT DOCUMENTS

| DE | 19702914 A1      | 9/1998  |
|----|------------------|---------|
| DE | 102004017956 A1  | 11/2005 |
| DE | 102006030530 A1  | 1/2008  |

* cited by examiner

*Primary Examiner* — Renee D Chavez
(74) *Attorney, Agent, or Firm* — Patentbar International, P.C.

(57) ABSTRACT

A method and an apparatus for examining a sample. The apparatus has a light source for generating excitation light in pulses which occur in succession at an excitation pulse frequency, for illuminating a sample region with the excitation pulse, and having a detector for detecting the detection light emanating from the sample region. The apparatus is characterized in that, for each detected photon of the detection light, the detector generates an electrical pulse and thereby a sequence of electrical pulses, and an analog-digital converter is provided that generates a digital data sequence by sampling the sequence of electrical pulses at a sampling rate.

30 Claims, 5 Drawing Sheets

METHOD AND APPARATUS FOR EXAMINING A SAMPLE

RELATED APPLICATIONS

This application claims priority to German Patent Application No. 10 2011 055 945.0, filed Dec. 1, 2011, which is incorporated herein by reference in its entirety.

FIELD OF THE INVENTION

The present invention relates to a method for examining a sample, as well as to an apparatus for carrying out the method.

BACKGROUND OF THE INVENTION

The present invention relates moreover to an apparatus for examining a sample, the apparatus having a light source for generating excitation light in pulses which occur in succession at an excitation pulse frequency, for illuminating a sample region with the excitation pulse, and having a detector for detecting the detection light emanating from the sample region.

To investigate the properties or the dynamic behavior of biological samples, many applications require that they be exposed to illuminating light in order to subsequently analyze the detection light emanating from the sample. Excitation light is often used to optically excite fluorescent dyes, for example, in order to subsequently investigate the properties of the fluorescent light emanating from the sample. Some examination methods call for using a pulsed light instead of a continuous light beam to illuminate the sample; for example for measuring the lifetime of an excitation state. It is namely possible, for example, to excite fluorescent dyes with short light pulses, in order to electronically measure the time delay of the emission light pulses. German Patent Application DE 10 2004 017 956 A1, for example, describes a microscope for analyzing the lifetime of excited states in a sample. The microscope includes at least one light source for generating excitation light and at least one detector for receiving detection light emanating from the sample. The microscope is characterized in that the light source includes a semiconductor laser which emits pulsed excitation light, an adjusting device being provided for adjusting the pulse repetition rate to the specific lifetime properties of the sample.

By analyzing the lifetime of the excited states of a sample labeled with one or more fluorescent dyes, important information can be obtained about the properties of the sample. In particular, information about a sample region being analyzed, such as information about the composition and surroundings thereof, can be obtained by using multiple fluorescent dyes with the aid of fluorescence lifetime imaging microscopy (FLIM). In cell biology, for example, the calcium concentration in a sample region can be indirectly inferred by measuring the lifetime of the fluorescent dyes.

SUMMARY OF THE INVENTION

Many applications require detecting individual photons and, depending on the individual case, thereby determining the number of detected photons or a time interval between an excitation pulse and one of the detection photons.

For each detected photon, detectors used for counting photons emit an electrical pulse. The electronics required for analyzing these electrical pulses, which are often in the form of PC plug-in cards, such as time measurement cards, are commercially available. However, apart from the high cost, such a time measurement card has the disadvantage of a very long dead time, so that, upon excitation of the sample, it is only able to detect the arrival of the first detection pulse (first detection photon) and is then "blind" for a significant period of time. Ultimately, a significant portion of the information contained in the detection light emanating from the sample remains hidden from the user. To be able to nevertheless perform the measurement, the user has no option other than to reduce the excitation power to a level where there is a low probability of photons arriving in rapid succession. To obtain a usable result, however, measurements must then be taken over a very lengthy period of time.

Even if the detector is generally suited for recording photons arriving in rapid succession, the curve shape of the electrical signal it generates resembles a superposition of the individual pulses, which in most cases overtaxes the electronic evaluation devices known heretofore.

Moreover, a high repetition rate of the excitation pulses and thus frequent measurements within one measurement period are not possible. The attainable measurement rate is actually far below the usual repetition rates of commercially available pulsed lasers. Therefore, a very long time is usually required to collect enough data to generate a FLIM image, for example.

Moreover, different evaluation electronics are needed for different applications, such as photon counting or FLIM applications, for example.

It is, therefore, an object of the present invention to provide a method that will make it possible to obtain more accurate measurement results in a shorter period of time.

This objective is achieved by a method that is characterized by the following steps:

a. generating excitation light in pulses which occur in succession at an excitation pulse frequency;

b. illuminating a sample region with the excitation light;

c. detecting the detection light emanating from the sample region using a detector which, for each detected photon of the detection light, generates an electrical pulse and thereby a sequence of electrical pulses; and d. generating a digital data sequence by sampling the sequence of electrical pulses at a sampling rate using an analog-digital converter.

It is, therefore, a further object of the present invention to provide an apparatus that will make it possible to obtain more accurate measurement results in a shorter period of time.

The further objective is achieved by an apparatus of the type mentioned at the outset which is characterized in that, in response to each detected photon of the detection light, the detector generates an electrical pulse and thereby a sequence of electrical pulses, and in that an analog-digital converter is provided that generates a digital data sequence by sampling the sequence of electrical pulses at a sampling rate.

It is, inter alia, a realization of the present invention that it is only possible to obtain information that goes beyond the instant of arrival of a first photon if the signal processing control device is also capable of detecting those photon events which occur after the arrival of the first photon, but which are to be associated with the same excitation pulse. It was also discovered that this may be achieved by immediately converting the analog measurement signals into sequences of digital numbers.

In particular, the present invention advantageously permits cyclically repeated measurements at a repetition frequency of 80 MHz and above, which corresponds to that of commercially available pulsed lasers. Moreover, more accurate information about the lifetime characteristics of the sample may be obtained since the high data processing speed, in particular, not only makes it possible for the time of arrival of the first photon to be detected at any one time, but nearly all photon events, provided there is sufficient excitation power. This is even the case when the photons arrive at the detector within a short time interval.

To achieve a satisfactory accuracy and a satisfactory time resolution, one special embodiment provides that the sampling rate be preferably significantly higher than the excitation pulse frequency. In particular, it may be provided that the sampling rate be more than 50 times greater than the excitation pulse frequency. For example, it may be provided that the sampling rate be greater than 1 gigasample per second, in particular, greater than 3 gigasamples per second, in particular, greater than 5 gigasamples per second.

In one practical embodiment, the sampling rate is approximately 5 gigasamples per second. The sampling may be advantageously carried out at a resolution of 8 bits or at a resolution of 10 bits. It is self-evident that an even higher sampling rate and/or sampling resolutions are possible. However, the analog-digital converter required for this purpose has a very high power consumption and generally a high cost.

One particular embodiment provides that the excitation pulse frequency be greater than 50 MHz, in particular, be equal to approximately 80 MHz, and/or that the duration of an excitation pulse frequency be shorter than 10 ps, in particular, shorter than 1 ps, in particular, shorter than 100 fs. This embodiment allows each light pulse to be fully utilized at the excitation pulse frequency of standard commercial lasers.

It has been found that, for most applications, the use of a pulsed light source having an excitation pulse frequency of approximately 80 MHz, as well as the use of an analog-digital converter having a sampling rate of 5 gigasamples per second at a resolution of 8 bits lead to very satisfactory measuring results.

One particular practical implementation of the method provides that the excitation light composed of primary light (for example, of a pulsed laser) be split off and that a portion of the primary light that differs from the excitation light be detected by an excitation detector which generates a further electrical pulse for each detected pulse and thereby a sequence of further electrical pulses. The further electrical pulses generated by the excitation detector may, in particular, be used as a power reference or time reference for the further measurement.

To this end, it may be provided, for example, for the electrical pulses and the further electrical pulses to be superposed, in particular, with opposite sign, and for the superposition signal to be sampled by the analog-digital converter to generate the digital data sequence. A superposition device, in particular a power combiner, may be used for the superposition. However, it is also fundamentally possible to sample the electrical pulses and the further electrical pulses in a different manner using the same analog-digital converter to generate the digital data sequence. When one single analog-digital converter is used, some resolution is generally lost in terms of amplitude. However, a time jitter is avoided, which may occur in the case of the fundamentally possible use of two different analog-digital converters for the electrical pulses, on the one hand, and the further electrical pulses, on the other hand.

Nevertheless, in some applications, where it is a question, in particular, of a good resolution in terms of the signal height, it is advantageous when the further data sequence is generated by sampling the further sequence of further electrical pulses, not using the analog digital converter that samples the sequence of electrical pulses originating from the detection light, rather by using another analog-digital converter having another sampling rate. The other sampling rate may be just as great as the sampling rate. However, it may also be provided that the sampling rates of the different analog-digital converters differ from one another. In particular, a more cost-effective embodiment may be used for the further analog digital converter, because, generally, the further sequence to be sampled includes well spaced electrical pulses.

An evaluation electronics is preferably used to process the digital data sequence and/or the further digital data sequence. One very reliable and rapid embodiment provides that the digital data sequence and/or the further digital data sequence be processed using an evaluation electronics whose design is at least partially based on a programmable integrated circuit, in particular a field programmable gate array (in short, FPGA).

In particular, to render possible a parallel processing of the data, one advantageous specific embodiment provides that the digital data sequence and/or the further digital data sequence be divided into data packets.

In an especially advantageous manner, the digital data sequence and/or the further digital data sequence may be divided into data packets, that each represent a measurement period that is at least as long, in particular, exactly as long as the time interval between successive excitation pulses, for example. Such an embodiment has the particular advantage of allowing exactly those measurement data that originate from the detection light caused by the optical excitation of each particular excitation pulse to be associated therewith.

Due to the large amount of data, it is often only possible to analyze the data in real time at considerable cost. An asynchronous analysis for acquiring data is fundamentally possible. To this end, one advantageous approach provides for analyzing the data in parallel, and for other additional data, for example, pertaining to the particular sample location, in particular pixels, or an additional time stamp to be associated with and/or added to the data packets into which the digital data sequence and/or the further digital data sequence are/is divided.

In particular, it may be provided that further data on the position of the sample location being examined in the particular case and/or on the corresponding pixel, and/or a time stamp and/or a consecutive number and/or different numbers be added in each case to the data packets. To make an evaluation simpler and more reliable, in particular, each data packet may also have the end of a preceding data packet and/or the beginning of the subsequent data packet appended thereto.

An asynchronous analysis may be carried out, in particular, in parallel structures, in particular in evaluation electronics whose design is based, for example, on programmable integrated circuits, in particular, field programmable gate arrays (in short, FPGA), in FPGA networks, but also in connected PC systems, and/or clusters of evaluation processors. It may also be provided for the analysis to take place in the processing units of graphic cards. In particular, the digital data sequence and/or the further digital data sequence and/or the data packets may be temporarily stored prior to the evaluation.

For example, to generate a FLIM image, it may be provided that the number of excitation pulses and/or the number of the detected photons be ascertained from each data packet, and/or that the number of excitation pulses per unit of time and/or the number of detected photons per unit of time be ascertained from the digital data sequence and/or the further digital data sequence.

In one particular embodiment, the instants of the excitation pulses and/or of the detected photons are ascertained from the data packets. In particular, it may be provided for the instants of the excitation pulses and/or of the detected photons to be determined from the digital data sequence and/or the further digital data sequence. When the method according to the present invention, respectively the apparatus according to the present invention are used in the field of FLIM technology, it is advantageous that a most accurate possible excitation be associated with each detection light pulse. For this purpose, one advantageous embodiment provides that the instant of the centroid of the recorded measurement curve or an extremum of the measurement curve be determined and used for the further evaluation. This may be done, for example, by making an approximation to a higher order polynomial or by performing a spline interpolation. The use of neural networks or a similarly suited classification is also considered.

In one especially exact embodiment, the electrical signals and/or the data sequence and/or the further data sequence and/or the data packets are filtered, in particular, to compensate for the frequency dependencies of the detector and/or of the analog electronics of the pulse amplifier. In particular, a digital filtering of the data sequence and/or of the further data sequence and/or of the data packets may be carried out. This makes it possible to compensate for the pulse amplifiers often being used in an AC voltage-coupled manner, so that a slow compensation drift is impressed upon the output signal when a fast pulse occurs.

One especially flexible specific embodiment provides for using at least one adaptive and/or adjustable filter. In particular, it may be advantageously provided for at least one adaptive and/or adjustable filter to be used that compensates for the aging and/or thermal effects of the detector and/or of the analog electronics.

In particular, with regard to a FLIM analysis, it may likewise be advantageously provided in each case for a time difference to be determined between the arrival of an excitation pulse at the sample region and the emission of a detection photon from the illuminated sample region. In particular, to achieve a particular accuracy, it may be advantageously provided for a frequency distribution of a plurality of computed time differences to be calculated.

An apparatus that is specifically designed for implementing a method according to the present invention is particularly advantageous.

One advantageous exemplary embodiment of an apparatus according to the present invention features a scanning device for directing the excitation light to different sample locations and/or for scanning a sample. In particular, a scanning device may be provided for directing the excitation light to different sample locations and/or for scanning a sample, a control device providing data and/or signals including location information regarding the particular position of the scanning device. These data may be used, on the one hand, to position an excitation light beam relative to the sample and, on the other hand, to be added to the generated data sequences and/or data packets, in particular, for the later identification and/or analysis thereof.

In one advantageous embodiment, the apparatus according to the present invention is part of a scanning microscope, in particular, of a confocal scanning microscope. Especially beneficial is also a scanning microscope having an apparatus according to the present invention, which may also be optionally retrofitted or subsequently added.

BRIEF DESCRIPTION OF THE DRAWINGS

Other objectives, advantages, features and possible applications of the present invention may be derived from the following description of an exemplary embodiment, which makes reference to the drawing. In this context, all of the described and/or illustrated features constitute the subject matter of the present invention, either alone or in any useful combination, and regardless of the manner in which they are combined in the claims or antecedents thereof.

In the drawing.

DETAILED DESCRIPTION OF THE PREFERRED EMBODIMENTS

Figure 1:
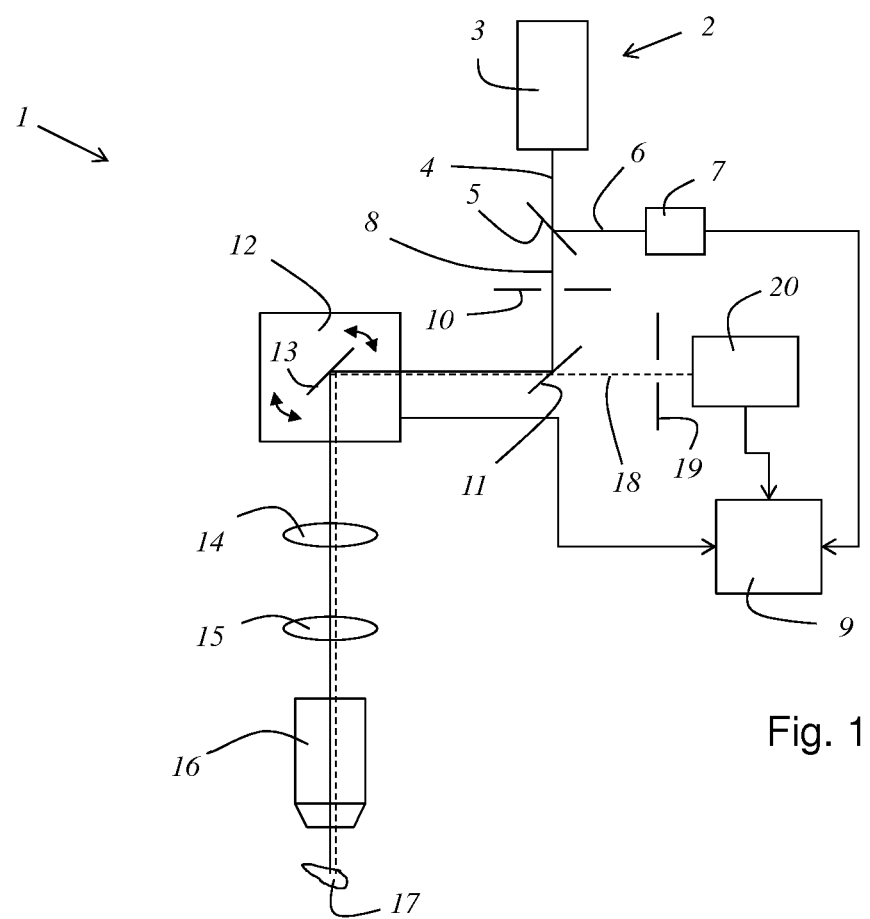
FIG. 1: shows an exemplary embodiment of a scanning microscope which features an apparatus according to the present invention.

FIG. 1 shows an exemplary embodiment of a scanning microscope 1 which features an apparatus according to the present invention. Scanning microscope 1 is designed as a confocal scanning microscope.

Scanning microscope 1 has a light source 2 which, as a pulsed laser 3 for generating excitation light, emits excitation pulses that occur in succession at an excitation pulse frequency. Specifically, pulsed laser 3 generates a primary light beam 4 that impinges upon a first beam splitter 5. There, primary light beam 4 is split into a measuring beam 6 and an excitation light beam 8.

Excitation light beam 8 passes through an illumination pinhole 10 and then arrives at main beam splitter 11.

This directs excitation light beam 8 to a scanning device 12 that includes a gimbal-mounted scanning mirror 13. Excitation light beam 8 subsequently arrives via scanning optical system 14 and tube optical system 15 and via microscope objective 16 at sample 17. There, a sample region is exposed to the excitation light, thereby optically exciting the fluorescent dyes present there.

Detection light 18 emanating from sample 17 reaches main beam splitter 11 along the same optical path along which excitation beam 8 traveled from main beam splitter 11 to sample 17, but in the opposite direction. It then passes through the main beam splitter and downstream detection pinhole 19, and finally reaches a detector 20, which, for each detected photon of detection light 18, generates an electrical pulse and thereby a sequence of electrical pulses. These are delivered to an evaluation and control device 9 which includes an electronic evaluation circuit having an analog-digital converter (not shown in this figure) and which generates a digital data sequence in that the analog-digital converter samples the sequence of electrical pulses, the sampling rate being greater than the excitation pulse frequency.

Measuring beam 6 is directed to an excitation director 7. Excitation detector 7 detects the portion of primary light beam 4 that differs from excitation light beam 8 and, for each detected pulse of the different portion of primary light 4, generates another electrical pulse and thereby a sequence of further electrical pulses. These are likewise delivered to evaluation and control device 9 which generates a further digital data sequence from the further electrical pulses in that another analog-digital converter samples at a sampling rate that is higher than the excitation pulse frequency.

Scanning device 12 transfers information on the particular position of scanning mirror 13 in the form of data to evaluation and control device 9. Control device 9 correlates this information with the respective data obtained from the first analog signal and the second analog signal in a manner that makes it possible to infer which sample location the particular data sequences and/or data packets belong to.

Figure 2:
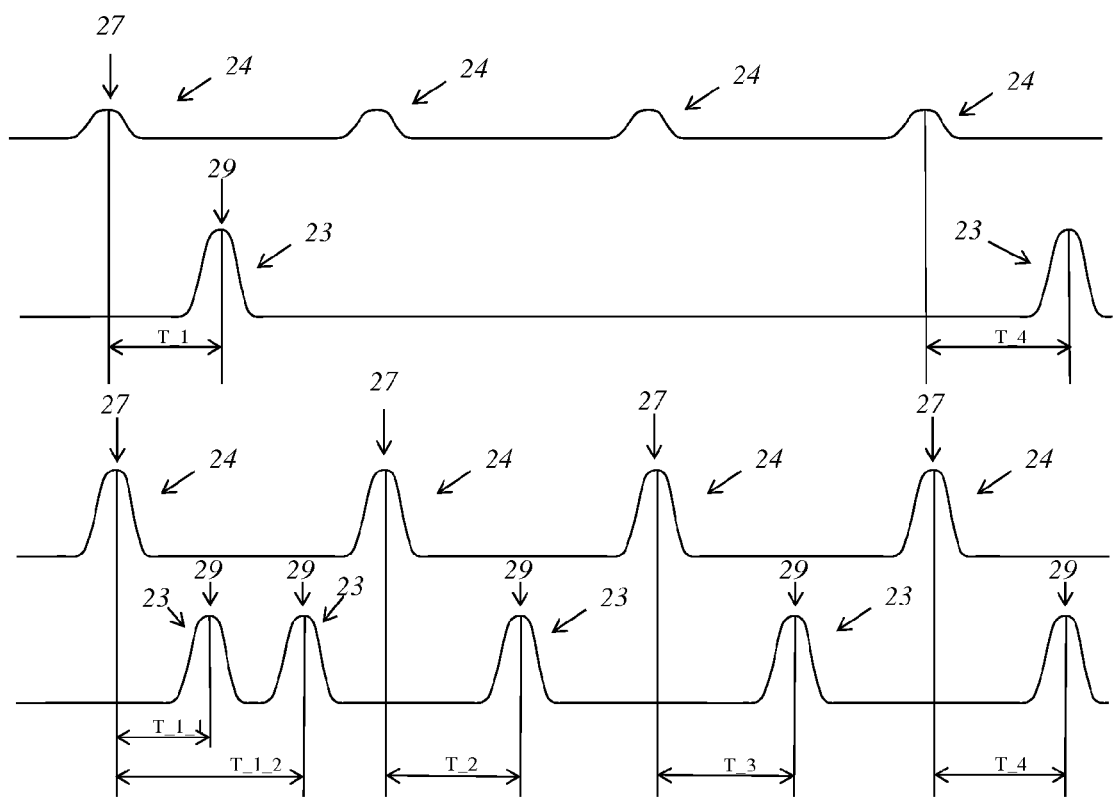
FIG. 2: is a representation of the time-power profile of the excitation light and of the detection light at a very low excitation power and at a high excitation power.

In the top half of FIG. 2, a sequence of further electrical pulses 24 is shown, whose power is proportional to the power of excitation light 8, and a sequence of electrical pulses 23, which are each generated by a detected photon, at a very low excitation power. It is discernible that merely a few electrical pulses 23, thus few photon events, are to be captured and detected because of the low emission probability, which is due to the low power of the excitation light. Generally, such a measuring situation can also be handled by prior art apparatuses. This does not necessarily apply to the situation shown in the bottom half of the illustration (high excitation power).

In the case of a high excitation power, the emission probability is so high that one excitation pulse 24 may even trigger several detection photons and thus several electrical pulses 23. The bottom half of the illustration shows the shape of the measurement curves when the time interval between successive electrical pulses 23 is greater than the pulse duration thereof.

Figure 3:
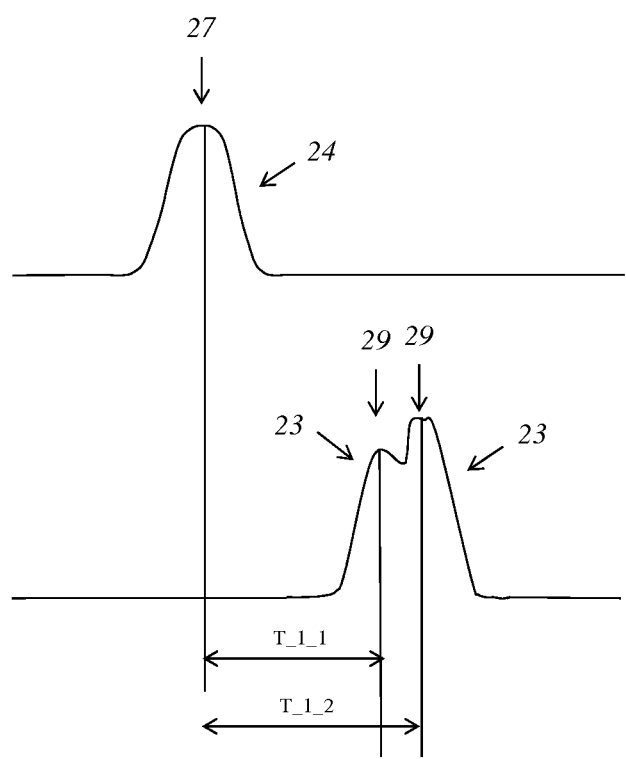
FIG. 3: shows a representation of the time-power profile of the excitation light and of the detection light in the case of rapidly successive photon events.

It may, however, also occur that two detection pulses are detected that are closely adjacent in time. The curve shape of the measurement curves is then essentially derived from the superposition of the individual signals. This is shown in FIG. 3. The present invention advantageously allows even such events to be recorded and analyzed.

Evaluation and control device 9 records instants 27 of further electrical pulses 24, which are generated substantially in synchronism with the excitation pulses, and instants 29 of electrical pulses 23, which originate from those of the detected photons. This may be accomplished, for example, by determining the centroids of the recorded curve shape or by approximation of a higher-order polynomial.

Figure 4:
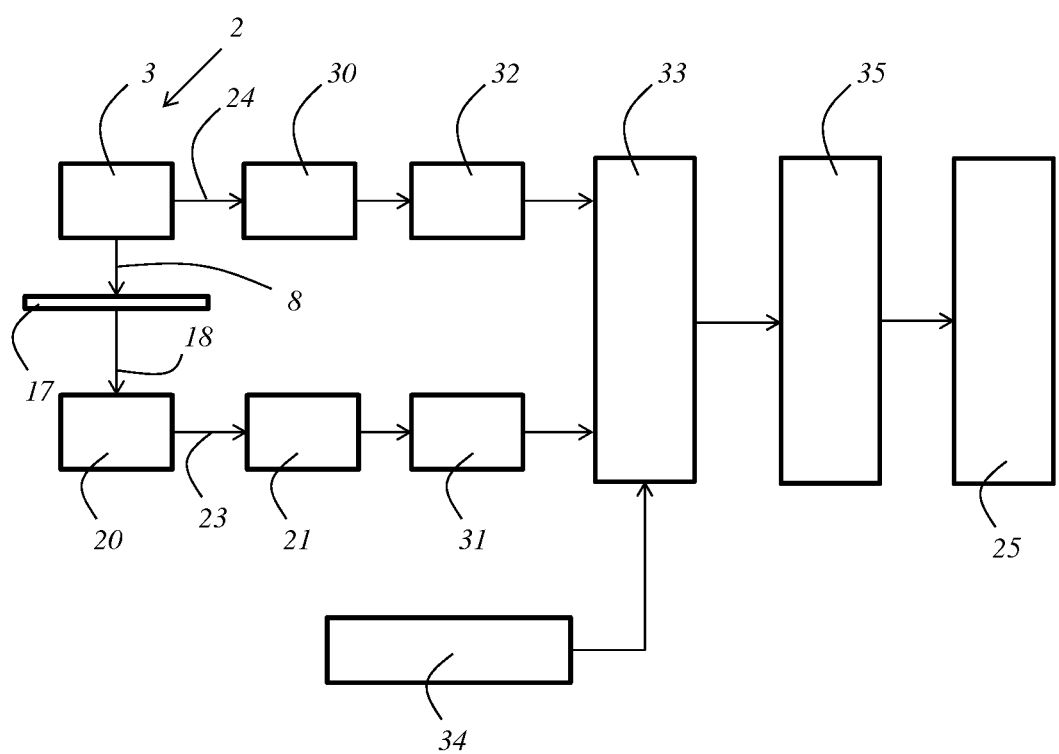
FIG. 4: is a schematic representation of an exemplary embodiment.

FIG. 4 schematically depicts an exemplary embodiment where the individual components are clearly represented as boxes. A sample 17 is illuminated by excitation light 8 which is from a light source 2 in the form of a pulsed laser 3 and whose excitation pulses occur in succession at an excitation pulse frequency of 80 MHz. Detection light 18 emanating from sample 17 is detected by a detector 20. For each detected photon of detection light 18, detector 18 generates an electrical pulse 23 and thereby a sequence of electrical pulses 23. The sequence of electrical pulses 23 is passed to a first amplifier 21, is amplified, and subsequently directed to a first analog-digital converter 31 which generates a digital data sequence by sampling the sequence of electrical pulses 23 at a sampling rate of 5 gigasamples per second.

Excitation light 8 is split off from the primary light. A portion 22 of the primary light that differs from excitation light 8 is detected by an excitation detector that generates a further electrical pulse and thereby a sequence of further electrical pulses 24 for each detected pulse of the different portion of the primary light. The sequence of electrical pulses 24 is passed to a further amplifier 30, is amplified, and subsequently directed to a further analog digital converter 32, which generates a further digital data sequence by sampling the further sequence of electrical pulses 24 at a sampling rate of 5 gigasamples per second.

The first digital data sequence and the further digital data sequence are subsequently delivered to a correlating unit 33 which divides the digital data sequence and the further digital data sequence into data packets which, in each case, represent a measurement period that is exactly as long as the time interval between successive excitation pulses. This has the particular advantage that exactly those measurement data that originate from the detection light caused by the optical excitation of each excitation pulse are simply associated with the excitation pulse. Moreover, in correlating unit 33, further data made available by a control unit 34 regarding the position of the sample location being examined in the particular case, a time stamp, as well as a consecutive number are added in each case to the data packets. In particular, the end of a preceding data packet and/or the beginning of the subsequent data packet may be additionally added. Here, the particular advantage is derived that the time sequence of the data packets may be thereby reconstructed at any time.

The number of the respective pulses and instants 27, 29 thereof, as well as the time intervals therebetween are subsequently determined in an analysis unit 35. Finally, the results of the analysis, such as, for example, the respective number of pulses per data packet, the frequency distributions thereof and the pulse counts, are stored in a memory unit 25.

Figure 5:
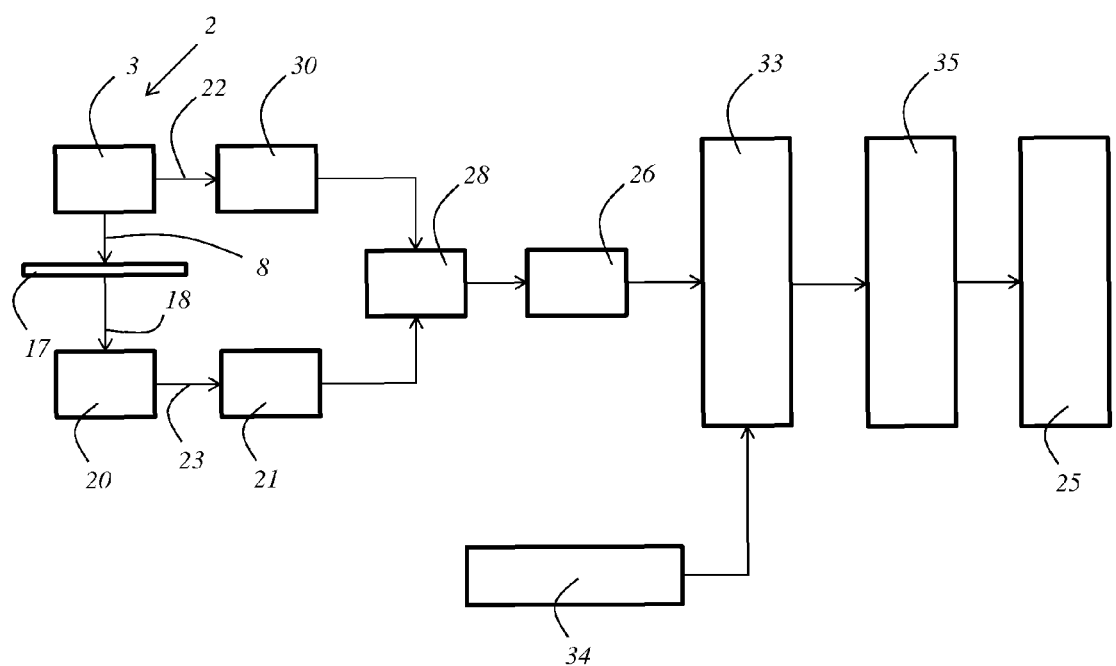
FIG. 5: is a schematic representation of another exemplary embodiment.

FIG. 5 shows a schematic representation of a further exemplary embodiment where the individual components are likewise illustrated as boxes for the sake of clarity. This variant differs from that shown in FIG. 4 in that the sequence of electrical pulses 24 and the further sequence of electrical pulses 23 are not sampled in the particular case by a separate analog-digital converter, but, to facilitate correlation, are first mutually superposed with opposite sign by a superposition device 28. The superposition signal is subsequently fed to an analog-digital converter 38 to generate a digital data sequence. Superposition device 28 is designed as a power combiner. In comparison to the device shown in FIG. 4, some resolution amplitude is actually generally lost here. However, a time jitter, which can occur in the case of the fundamentally possible use of two different analog-digital converters for the electrical pulses, on the one hand, and the further electrical pulses, on the other hand, is avoided.

Analogously to the device shown in FIG. 4, the digital data sequence is subsequently passed to a correlating unit 33 that divides the digital data sequence into data packets, which each represent a measurement period that it exactly as long as the time interval between successive excitation pulses.

There, further data made available by a control unit 34 and regarding the position of the sample location being examined in the particular case, a time stamp, as well as a consecutive number are added in each case to the individual data packets. The number of the respective pulses and instants 27, 29 thereof, as well as the time intervals therebetween are subsequently determined in an analysis unit 35. Finally, results of the analysis, such as the respective number of pulses per data packet, the frequency distributions thereof and the pulse counts, for example, are stored in a memory unit 25.

LIST OF REFERENCE NUMERALS 1 scanning microscope
2 light source
3 pulsed laser
4 primary light beam
5 first beam splitter
6 measuring beam
7 excitation detector
8 excitation beam
9 evaluation and control device
10 illumination pinhole
11 main beam splitter
12 scanning device
13 scanning mirror
14 scanning optical system
15 tube optical system
16 microscope objective
17 sample
18 detection light
19 detection pinhole
20 detector
21 first amplifier
22 different portion of primary light beam 4
23 electrical pulses
24 further electrical pulses
25 memory unit
26 analog-digital converter
27 instants of further electrical pulses 24
28 superposition device
29 instants 29 of electrical pulses 23
30 further amplifiers
31 first analog-digital converter
32 further analog-digital converters
33 correlating unit
34 control unit
35 analysis unit

What is claimed is:

1. A method for examining a sample comprising:
generating excitation light in pulses which occur in succession at an excitation pulse frequency;
illuminating a sample region with the excitation light;
detecting detection light emanating from the sample region using a detector which for each detected photon of the detection light, generates an electrical pulse and thereby a sequence of electrical pulses; and
generating a digital data sequence by sampling the sequence of electrical pulses using an analog-digital converter at a sampling rate,
wherein the excitation light is split off from a primary light, and a portion of the primary light that differs from the excitation light is detected by an excitation detector which generates a further electrical pulse for each detected pulse of the different portion of primary light and thereby a sequence of further electrical pulses, and
wherein the electrical pulses and the further electrical pulses are superposed with opposite sign by a superposition device being a power combiner to provide a superposition signal which is sampled by the analog-digital converter to generate the digital data sequence, or the electrical pulses and the further electrical pulses are superposed with opposite sign by the power combiner to provide the superposition signal which is sample by the analog-digital converter to generate the digital data sequence.

2. The method as recited in claim 1, wherein the sampling rate is greater than 1 gigasample per second, the excitation pulse frequency is greater than 50 MHz or the sampling is carried out at a resolution of 8 bits or at a resolution of 10 bits.

3. The method as recited in claim 1, wherein the excitation pulse frequency is 80 MHz, or a duration of an excitation pulse is less than 10 ps (picoseconds).

4. The method as recited in claim 1, wherein a further digital data sequence is generated by another analog-digital converter sampling the further sequence of further electrical pulses at another sampling rate.

5. The method as recited in claim 4, wherein
a. a number of excitation pulses or a number of detected photons is ascertained from each data packet, or
b. a number of excitation pulses per unit of time or a number of detected photons per unit of time are ascertained from the digital data sequence or from the further digital data sequence.

6. The method as recited in claim 4, wherein instants of the excitation pulses or of the detected photons are ascertained from the data packets, or instants of the excitation pulses or of the detected photons are determined from the digital data sequence or from the further digital data sequence.

7. The apparatus as recited in claim 4, further comprising the step of digitally filtering the data sequence, the further data sequence or the data packets.

8. The method as recited in claim 1, wherein an evaluation electronics having a field programmable gate array is used to process the digital data sequence or the further digital data sequence.

9. The method as recited in claim 1, further comprising the step of filtering the electrical pulses or the further electrical pulses.

10. The method as recited in claim 9, wherein at least one adaptive or adjustable filter is used that compensates for aging or thermal effects of the detector or the analog-digital converter.

11. The method as recited in claim 1, wherein a time difference between arrival of an excitation pulse at the sample region and emission of a detection photon from an illuminated sample region is determined.

12. The method as recited in claim 11, wherein a frequency distribution of a plurality of computed time differences is calculated.

13. An apparatus for implementing a method according to claim 1.

14. A method for examining a sample comprising:
generating excitation light in pulses which occur in succession at an excitation pulses frequency;
illuminating a sample region with the excitation light;
detecting the excitation light emanating from the sample region using a detector which for each detected photon of the excitation light, generates an electrical pulse and thereby a sequence of electrical pulses; and
generating a digital data sequence by sampling the sequence of electrical pulses using an analog-digital converter at a sampling rate,
wherein the excitation light is split off from a primary light, and a portion of the primary light that differs from the excitation light it is detected by an excitation detector which generates a further electrical pulse for each detected pulse of the different portion of primary light and thereby a sequence of further electrical pulses, wherein a further digital data sequence is generated by another analog-digital converter sampling the further sequence of further electrical pulses at another sampling rate, and wherein the digital data sequence or the further digital data sequence is divided into data packets which each represent a measurement period that is at least as long as a time interval between successive excitation pulses, or the digital data sequence or the further digital data sequence is divided into data packets which are each associated with different sample locations represented as pixels.

15. The method as recited in claim 14, wherein further data is added to the data packets, said further data comprising a position of a sample location being examined, or a time stamp or a consecutive number or a different number added to the data packets and an end of a preceding data packet or a beginning of a subsequent data packet is appended to each data packet.

16. An apparatus for examining a sample, the apparatus having a light source for generating excitation light in pulses which occur in succession at an excitation pulse frequency, for illuminating a sample region with the excitation light, and having a detector for detecting light emanating from the sample region, wherein, for each detected photon of the detected light, the detector generates an electrical pulse and thereby a sequence of electrical pulses, and an analog-digital converter is provided that generates a digital data sequence by sampling the sequence of electrical pulses at a sampling rate, wherein the excitation light is split off from a primary light, and an excitation detector is providing which detects a portion of the primary light that differs from the excitation light and which generates a further electrical pulse and thereby a sequence of further electrical pulses for each detected pulse, wherein a further analog-digital converter is provided that generates a further digital data sequence by sampling the further sequence of further electrical pulses at another sampling rate, wherein an evaluation electronics device based on a field programmable gate array processes the digital data sequence or the further digital data sequence, and wherein the evaluation electronics device divides the digital data sequence or the further digital data sequence into data packets which each represent a measurement period that is at least as long as a time interval between successive excitation pulses, or the evaluation electronics device divides the digital data sequence or the further digital data sequence into data packets which are each associated with different pixel sample locations.

17. The apparatus as recited in claim 16, wherein the sampling rate is higher than the excitation pulse frequency, or the sampling rate is greater than 1 gigasample per second, or the excitation pulse frequency is greater than 50 MHz, or the sampling is carried out at a resolution of either 8 bits or 10 bits.

18. The apparatus as recited in claim 16, wherein the excitation pulse frequency is greater than 50 MHz or a duration of an excitation pulse is less than 10 picoseconds.

19. The apparatus as recited in claim 18, further comprising a scanning device for directing the excitation light to different sample locations or for scanning a sample, and a the control device providing data or signals that include location information regarding a position of the scanning device.

20. The apparatus as recited in claim 16, further comprising a superposition device being a power combiner to superpose the electrical pulses and the further electrical pulses with opposite signs, wherein the analog-digital converter samples the superposition signal to generate the digital data sequence, or the analog-digital converter samples the electrical pulses and the further electrical pulses to generate the digital data sequence.

21. The apparatus as recited in claim 16, wherein the evaluation electronics device adds further data to each data packet on a position of a sample location being examined or on a corresponding pixel, or a time stamp or a consecutive number or a different number.

22. The apparatus as recited in claim 16, wherein the evaluation electronics device determines a number of excitation pulses or a number of detected photons from each data packet, or the number of excitation pulses per unit of time or a number of detected photons per unit of time from the digital data sequence or from the further digital data sequence.

23. The apparatus as recited in claim 16, wherein the evaluation electronics device determines instants of the excitation pulses or the detected photons from the data packets, or instants of the excitation pulses or the detected photons from the digital data sequence or from the further digital data sequence.

24. The apparatus as recited in claim 16, wherein a digital filter filters the electrical signals or the further electrical signals.

25. The apparatus as recited in claim 24, wherein the filter is adaptive or adjustable or compensates for aging or thermal effects of the detector or the analog-digital converter.

26. The apparatus as recited in claim 16, wherein the evaluation electronics device determines a time difference between an arrival of an excitation pulse at the sample region and an emission of a detection photon from the illuminated sample region.

27. The apparatus as recited in claim 16, wherein the evaluation electronics device calculates a frequency distribution of a plurality of computed time differences.

28. The apparatus as recited in claim 16, wherein the apparatus is part of a confocal scanning microscope.

29. A scanning microscope comprising an apparatus according claim 16.

30. The apparatus as recited in claim 16, wherein a digital filter filters the data sequence, or the further data sequence, or the data packets.

* * * * *